US009831412B2

United States Patent
Ito

(10) Patent No.: US 9,831,412 B2
(45) Date of Patent: Nov. 28, 2017

(54) ULTRASOUND VIBRATION DEVICE, METHOD OF MANUFACTURING ULTRASOUND VIBRATION DEVICE, AND ULTRASOUND MEDICAL APPARATUS

(71) Applicant: OLYMPUS CORPORATION, Tokyo (JP)

(72) Inventor: Hiroshi Ito, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 530 days.

(21) Appl. No.: 14/611,361

(22) Filed: Feb. 2, 2015

(65) Prior Publication Data

US 2015/0145379 A1   May 28, 2015

Related U.S. Application Data

(63) Continuation of application No. PCT/JP2013/065968, filed on Jun. 10, 2013.

(30) Foreign Application Priority Data

Aug. 3, 2012 (JP) ................................. 2012-173033

(51) Int. Cl.
*H01L 41/047* (2006.01)
*H01L 41/09* (2006.01)
(Continued)

(52) U.S. Cl.
CPC .. *H01L 41/0471* (2013.01); *A61B 17/320092* (2013.01); *A61N 7/00* (2013.01);
(Continued)

(58) Field of Classification Search
CPC ................................. B41J 2/161; B41J 2/1623
(Continued)

(56) References Cited

U.S. PATENT DOCUMENTS 5,695,510 A    12/1997  Hood
2005/0099096 A1  5/2005  Baumgartner et al.
(Continued)

FOREIGN PATENT DOCUMENTS

JP          04096285 A  *  3/1992  ............. H01L 41/09
JP      2002-048552 A      2/2002
(Continued)

OTHER PUBLICATIONS

International Search Report dated Aug. 6, 2013 issued in PCT/JP2013/065968.
(Continued)

*Primary Examiner* — Thomas Dougherty
(74) *Attorney, Agent, or Firm* — Scully, Scott, Murphy & Presser, P.C.

(57) ABSTRACT

An ultrasound vibration device is provided with a stacked transducer in which a plurality of piezoelectric single crystal element layers are stacked between two metal blocks. Since each of the two metal blocks and the plurality of piezoelectric single crystal element layers is fusion-bonded relative to a stack direction by bonding metal having a melting point corresponding to half a Curie point of the plurality of piezoelectric single crystal element layers or below, it is possible to use non-lead material, reduce a processing cost and realize inexpensiveness.

9 Claims, 15 Drawing Sheets

(51) Int. Cl.
  *B06B 1/06* (2006.01)
  *A61B 17/32* (2006.01)
  *A61N 7/00* (2006.01)
  *H01L 41/083* (2006.01)
  *H01L 41/277* (2013.01)
  *A61B 17/28* (2006.01)
  *A61B 17/285* (2006.01)
  *A61B 17/29* (2006.01)
  *A61B 18/00* (2006.01)

(52) U.S. Cl.
  CPC ........ *B06B 1/0611* (2013.01); *H01L 41/0477* (2013.01); *H01L 41/083* (2013.01); *H01L 41/0833* (2013.01); *H01L 41/277* (2013.01); *A61B 17/282* (2013.01); *A61B 17/285* (2013.01); *A61B 2017/2925* (2013.01); *A61B 2018/00607* (2013.01); *Y10T 29/42* (2015.01)

(58) Field of Classification Search
  USPC .......................................... 310/328, 363–366
  See application file for complete search history.

(56) References Cited

U.S. PATENT DOCUMENTS

| | | | |
|---|---|---|---|
| 2007/0262679 A1 | 11/2007 | Maruyama et al. | |
| 2007/0269667 A1* | 11/2007 | Kobayashi | H01L 41/0838 428/469 |
| 2012/0236461 A1* | 9/2012 | Yamamoto | H01C 1/14 361/305 |

FOREIGN PATENT DOCUMENTS

| | | |
|---|---|---|
| JP | 2003-057035 A | 2/2003 |
| JP | 2009-000586 A | 1/2009 |
| JP | 2009-220014 A | 10/2009 |
| JP | 4388409 B2 | 12/2009 |

OTHER PUBLICATIONS

English Abstract of JP 2005-308691 dated Nov. 4, 2005.
Extended Supplementary European Search Report dated Feb. 1, 2016 from related European Application No. 13 82 6235.7.

* cited by examiner

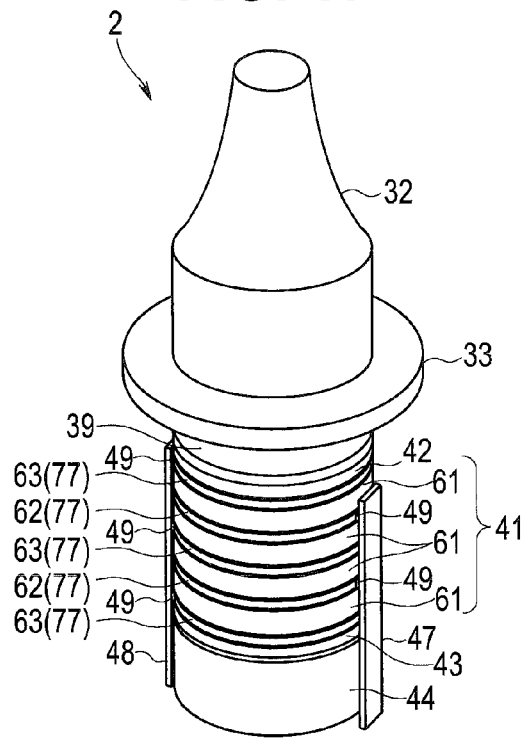
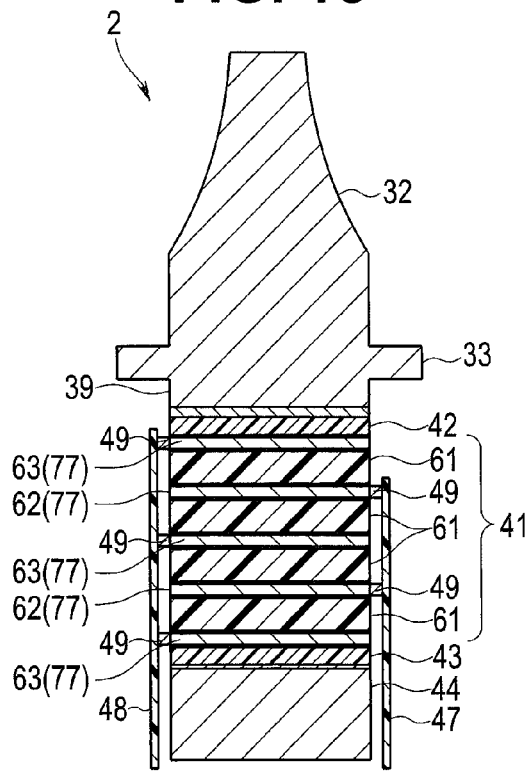

ULTRASOUND VIBRATION DEVICE, METHOD OF MANUFACTURING ULTRASOUND VIBRATION DEVICE, AND ULTRASOUND MEDICAL APPARATUS

CROSS REFERENCE TO RELATED APPLICATION

This application is a continuation application of PCT/JP2013/065968 filed on Jun. 10, 2013 and claims benefit of Japanese Application No. 2012-173033 filed in Japan on Aug. 3, 2012, the entire contents of which are incorporated herein by this reference.

BACKGROUND OF INVENTION

1. Field of the Invention

The present invention relates to an ultrasound vibration device which excites ultrasound vibration, a method of manufacturing the ultrasound vibration device, and an ultrasound medical apparatus provided with the ultrasound vibration device.

2. Description of the Related Art

Recently, ultrasound medical apparatuses include, for example, an ultrasound treatment instrument for performing coagulation/dissection treatment of living tissue. The ultrasound treatment instrument is provided with an ultrasound transducer which generates ultrasound vibration.

Some of conventional ultrasound treatment instruments internally include a bolted Langevin transducer, for example, as shown in Japanese Patent Application Laid-Open Publication No. 2009-220014, in a handpiece as an ultrasound transducer (vibration source). In such a conventional bolted Langevin transducer, a piezoelectric element which converts an electric signal to mechanical vibration is firmly fastened with a bolt and integrated with a front mass and a back mass which are constituted by metallic members, being sandwiched between the front mass and the back mass, and a whole vibrates as an integrated body.

Note that such a transducer that a piezoelectric element is sandwiched between metallic members and vibrates being integrated with the metallic members by some method including adhesion and the like is referred to as a Langevin transducer, and a Langevin transducer adopting fastening with a bolt as an integration method is referred to as a bolted Langevin transducer. As a general configuration, lead zirconate titanate (PZT: $Pb(Zr_x,Ti_{1-x})O_3$) is used for the piezoelectric element; the piezoelectric element is formed in a ring shape; and a bolt is inserted through an inside of the ring.

Because being highly productive and having a high electromechanical conversion efficiency and excellent characteristics as piezoelectric material, PZT as such a piezoelectric element has been used for various fields, such as an ultrasound transducer and actuator fields, for a long time.

SUMMARY OF THE INVENTION

An ultrasound vibration device of an aspect of the present invention is an ultrasound vibration device comprising a stacked transducer in which a plurality of piezoelectric single crystal element layers are stacked between two metal blocks, wherein at least each of the plurality of piezoelectric single crystal element layers is fusion-bonded relative to a stack direction by bonding metal having a melting point corresponding to half a Curie point of the plurality of piezoelectric single crystal element layers or below.

A method of manufacturing an ultrasound vibration device of an aspect of the present invention is a method of manufacturing an ultrasound vibration device including a stacked transducer in which a plurality of piezoelectric single crystal element layers are stacked between two metal blocks, wherein the two metal blocks and each of the plurality of piezoelectric single crystal element layers are fusion-bonded relative to a stack direction by bonding metal having a melting point corresponding to half a Curie point of the plurality of piezoelectric single crystal element layers or below, the method including: forming a block body in which respective stack materials are integrated by fusion bonding by slowly cooling a stacked body in which a first metal block of the two metal blocks, the plurality of piezoelectric single crystal wafers, and a second metal block of the two metal blocks are stacked by providing the bonding metal therebetween respectively after heating the stacked body to be at a melting point of the bonding metal; cutting out a plurality of columnar bodies from the bonded block body by machining; and machining a horn for amplifying ultrasound vibration on a portion of the first metal block of the columnar body.

Furthermore, an ultrasound medical apparatus of an aspect of the present invention is provided with: an ultrasound vibration device comprising a stacked transducer in which a plurality of piezoelectric single crystal element layers are stacked between two metal blocks, wherein the two metal blocks and each of the plurality of piezoelectric single crystal element layers are fusion-bonded relative to a stack direction by bonding metal having a melting point corresponding to half a Curie point of the plurality of piezoelectric single crystal element layers or below; and a probe distal end portion to which ultrasound vibration generated by the ultrasound vibration device is transmitted and which treats living tissue.

According to the present invention described above, it is possible to provide an ultrasound vibration device which can be fabricated at a low cost by reducing a processing cost of piezoelectric single crystal which is non-lead, a method of manufacturing the ultrasound vibration device, and an ultrasound medical apparatus provided with the ultrasound vibration device.

BRIEF DESCRIPTION OF THE DRAWINGS

FIG. 17 is a perspective view showing an ultrasound transducer on which FPCs are connected to electrodes, according to the second embodiment of the present invention;

FIG. 18 is a cross-sectional view showing the ultrasound transducer on which the FPCs are connected to the electrodes, according to the second embodiment of the present invention;

DETAILED DESCRIPTION OF THE PREFERRED EMBODIMENT(S)

The present invention will be described below with use of diagrams. Note that, in the description below, it should be noticed that drawings based on each embodiment are schematic, and a relationship between thickness and width of each portion, a ratio of thicknesses of respective portions, and the like are different from actual ones. There may be a case where such a part is included that a mutual dimensions relationship or ratio among the drawings is different from actual one.

First Embodiment

First, a first embodiment of the present invention will be described below on a basis of drawings.

Figure 1:
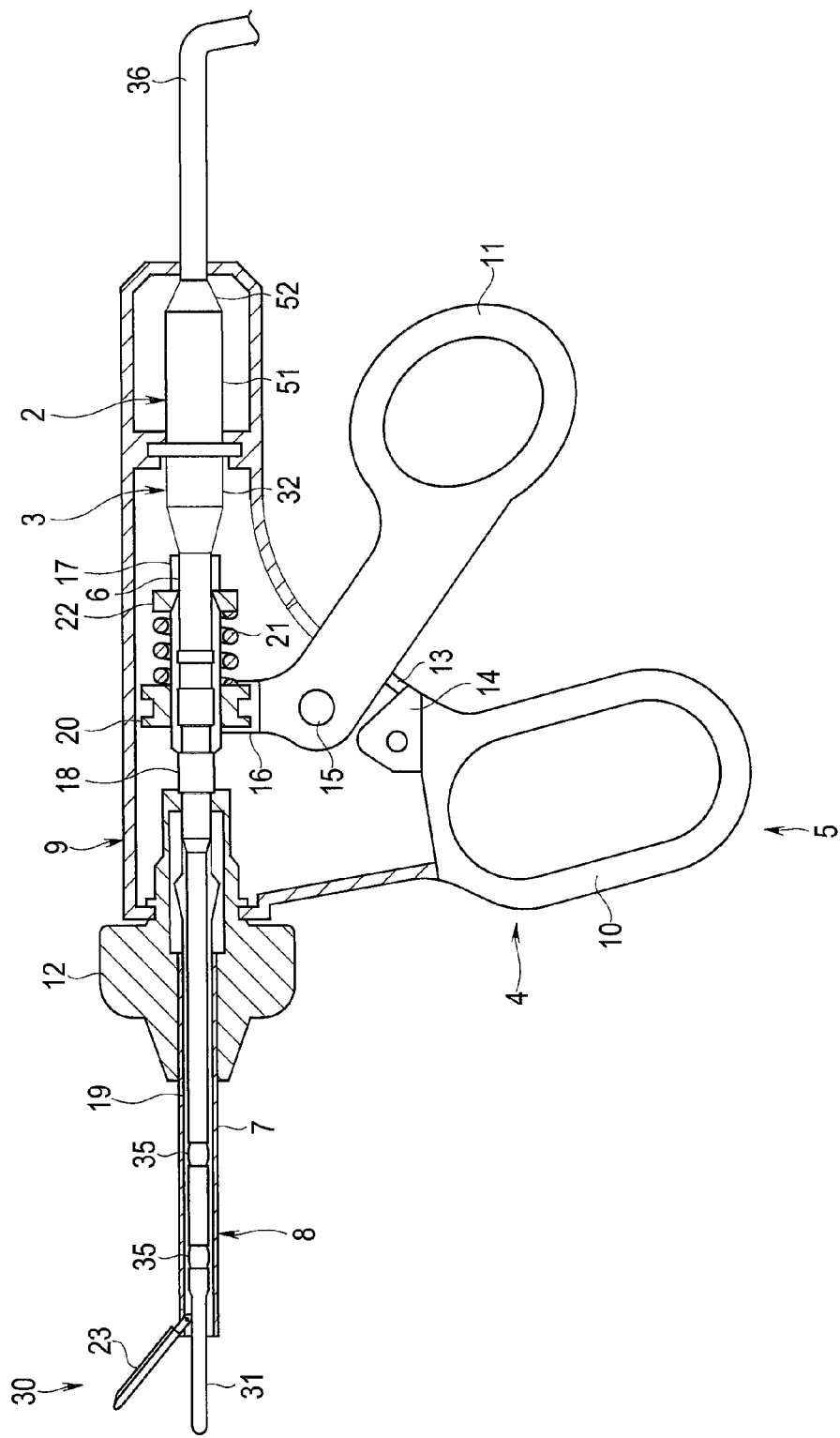
FIG. 1 is a cross-sectional view showing an overall configuration of an ultrasound medical apparatus according to a first embodiment of the present invention.
Figure 2:
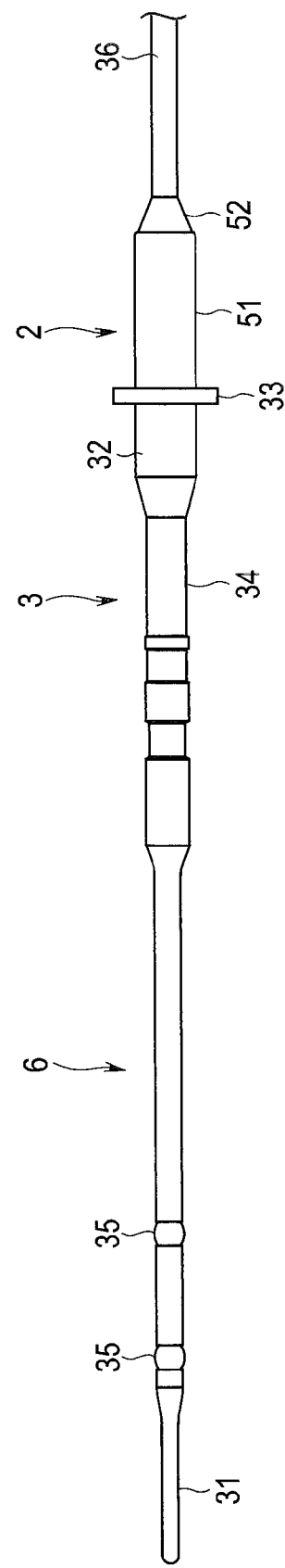
FIG. 2 is a diagram showing a schematic configuration of a whole transducer unit according to the first embodiment of the present invention.
Figure 3:
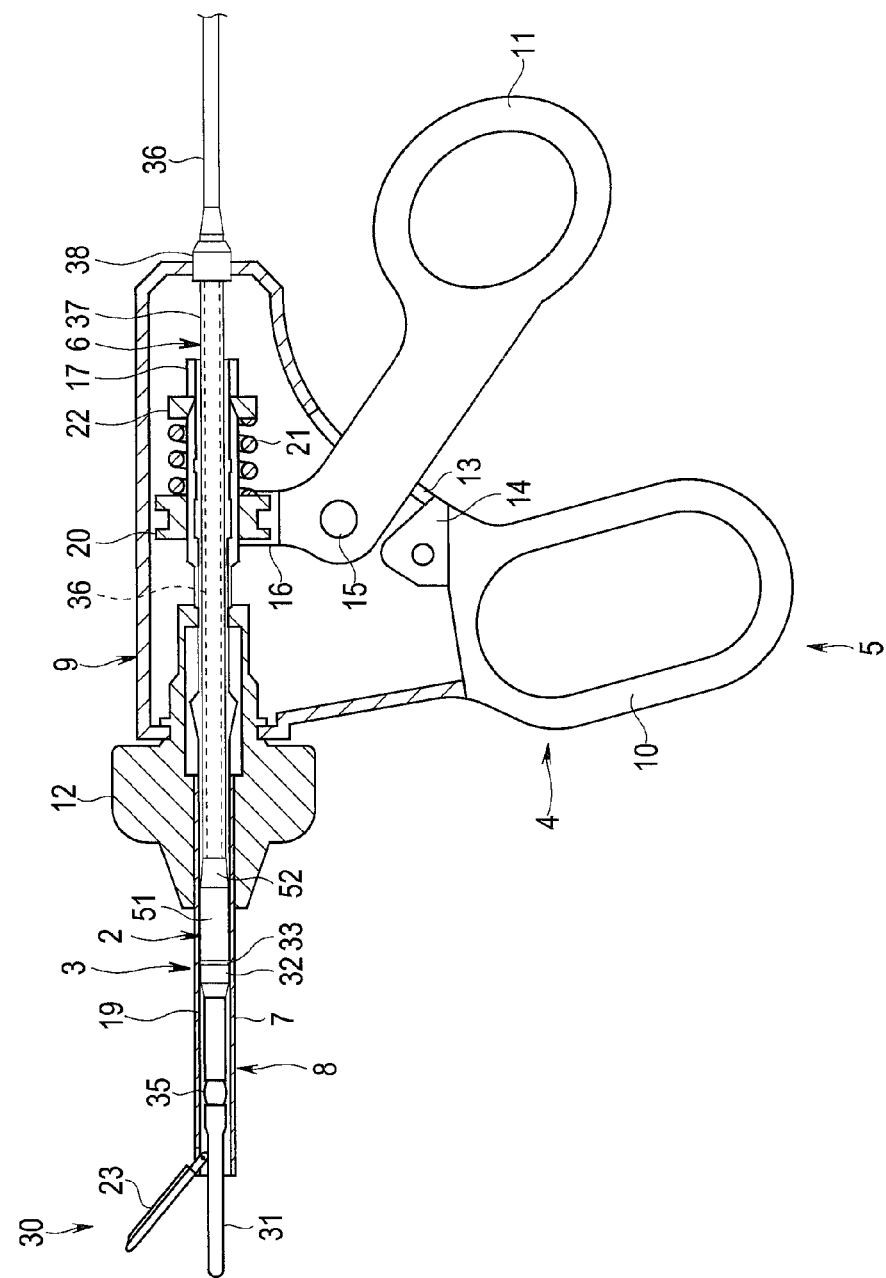
FIG. 3 is a cross-sectional view of an overall configuration of an ultrasound medical apparatus of another aspect according to the first embodiment of the present invention.
Figure 4:
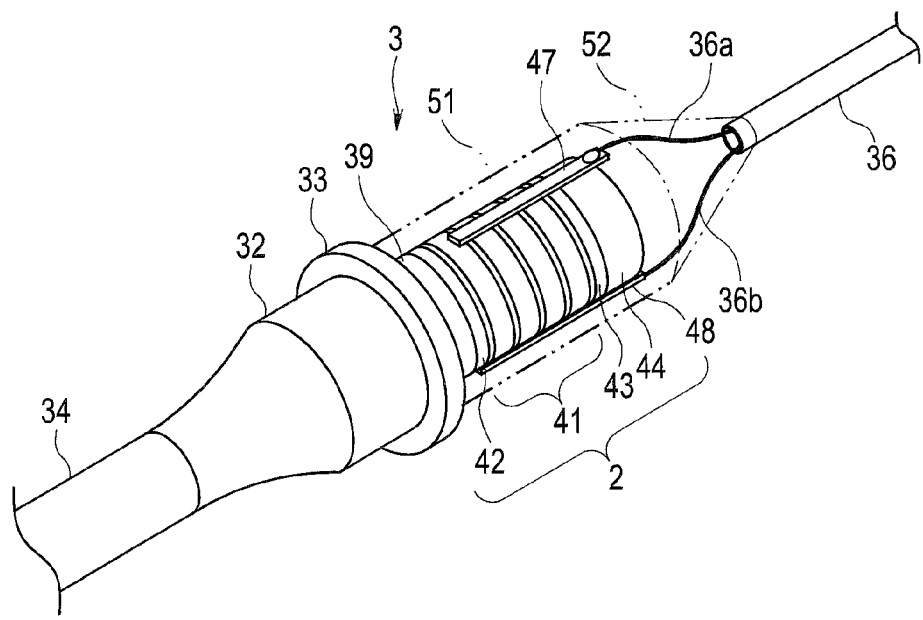
FIG. 4 is a perspective view showing a configuration of an ultrasound transducer according to the first embodiment of the present invention.
Figure 5:
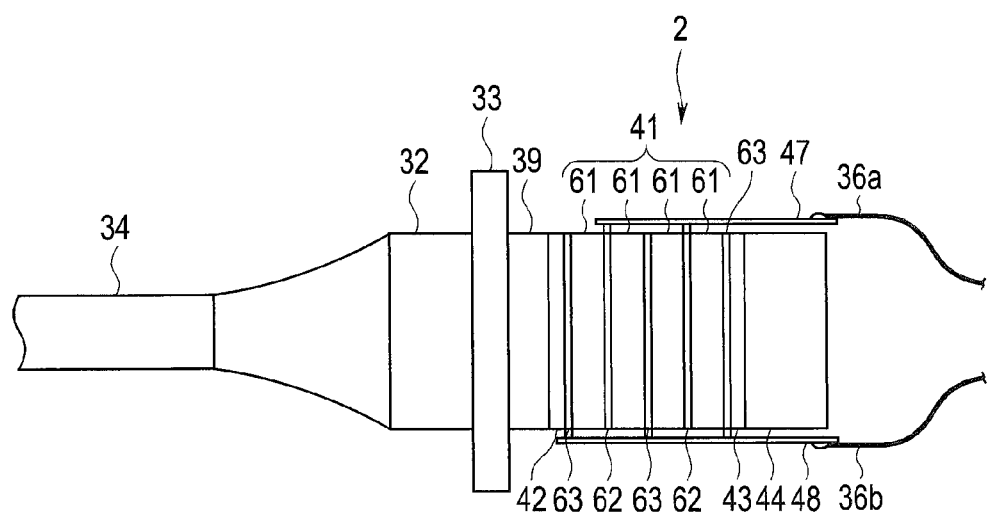
FIG. 5 is a cross-sectional view showing the configuration of the ultrasound transducer according to the first embodiment of the present invention.
Figure 6:
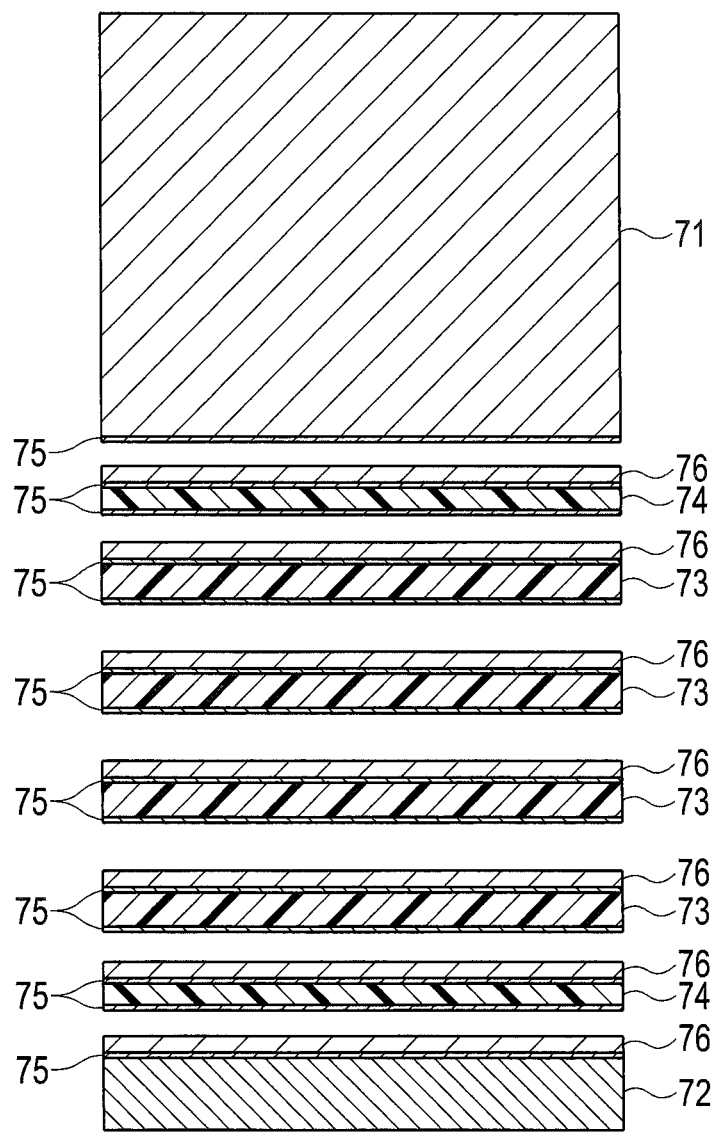
FIG. 6 is a cross-sectional view showing a configuration with various kinds of stack materials according to the first embodiment of the present invention.
Figure 7:
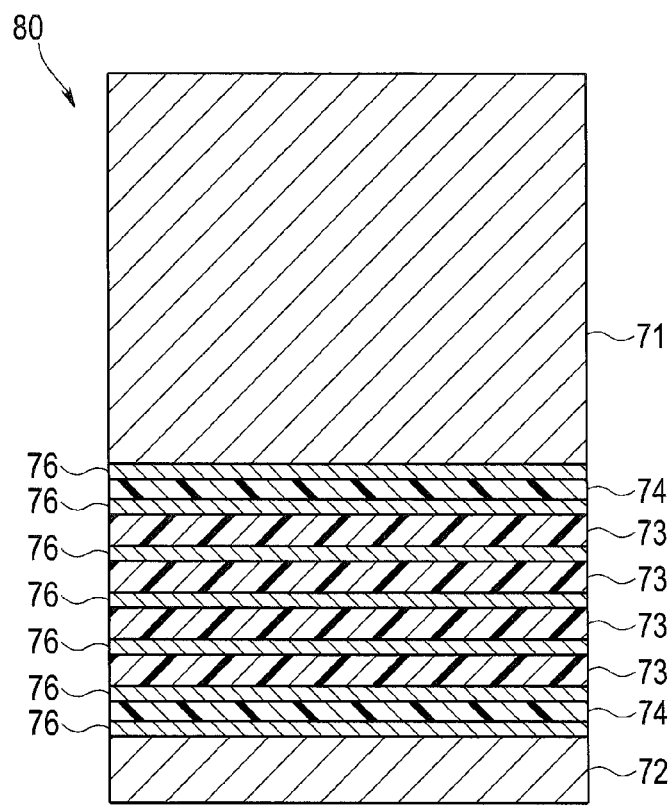
FIG. 7 is a cross-sectional view showing a bonded block body obtained by the various kinds of stack materials being bonded with one another, according to the first embodiment of the present invention.
Figure 8:
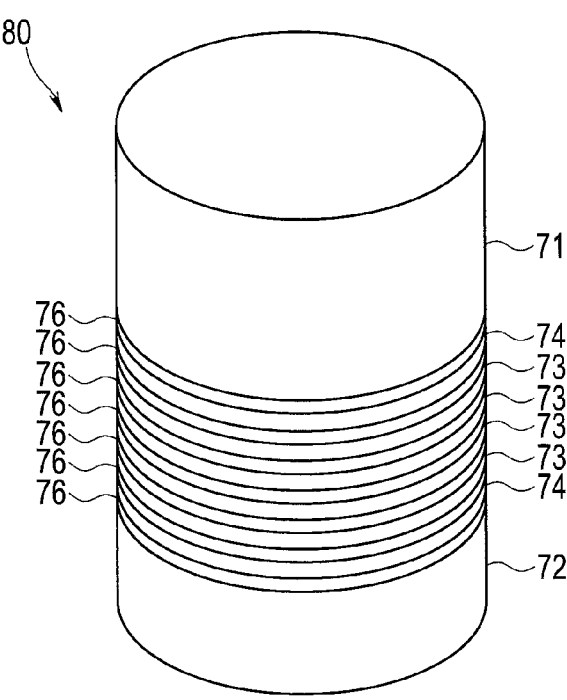
FIG. 8 is a perspective view showing the bonded block body obtained by the various kinds of stack materials being bonded with one another, according to the first embodiment of the present invention.
Figure 9:
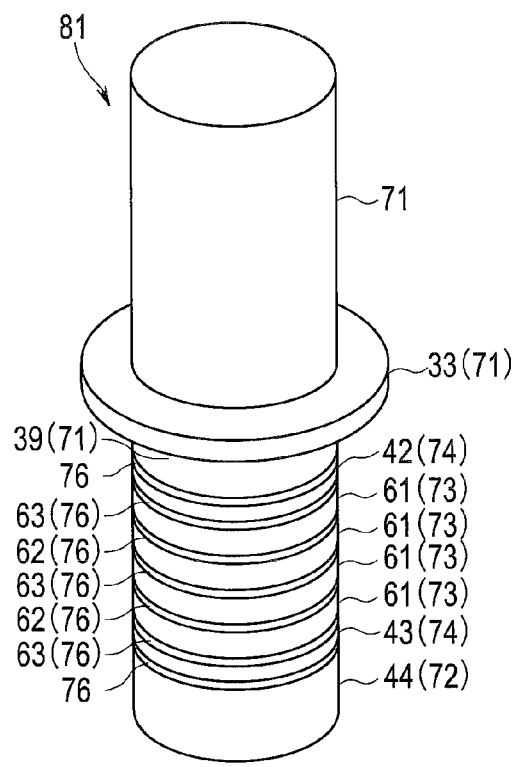
FIG. 9 is a perspective view showing a bonded columnar body cut out from the bonded block body according to the first embodiment of the present invention.
Figure 10:
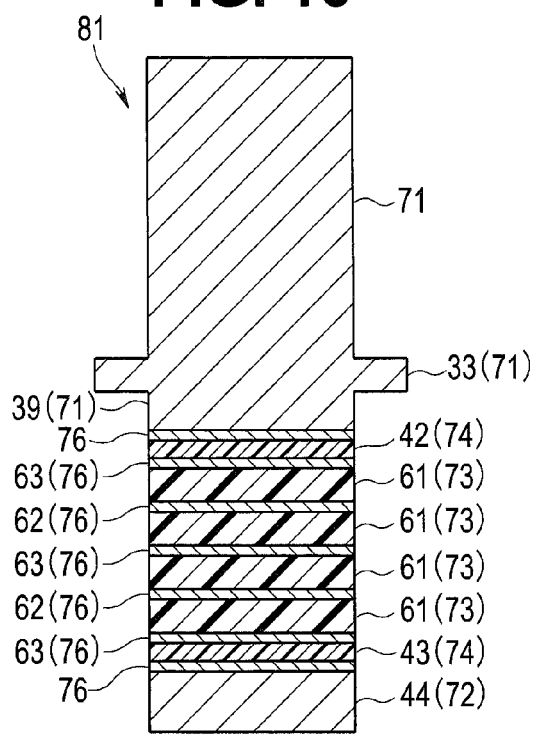
FIG. 10 is a cross-sectional view showing the bonded columnar body according to the first embodiment of the present invention.
Figure 11:
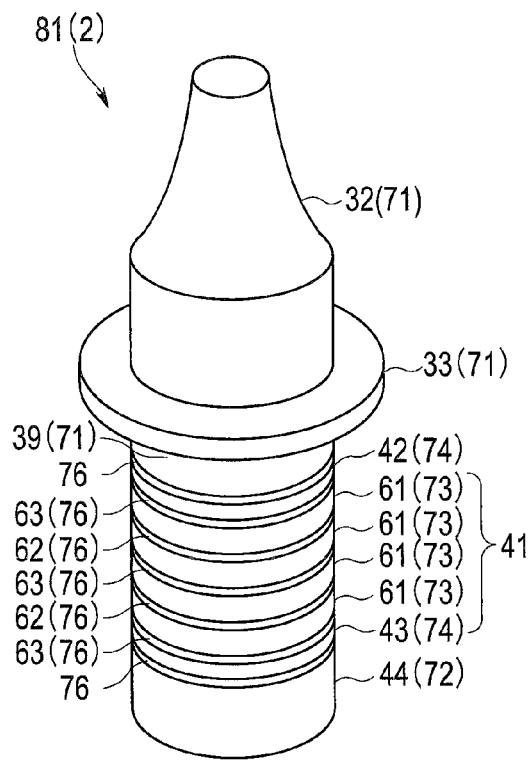
FIG. 11 is a perspective view showing the ultrasound transducer with a horn formed from the bonded columnar body, according to the first embodiment of the present invention.
Figure 12:
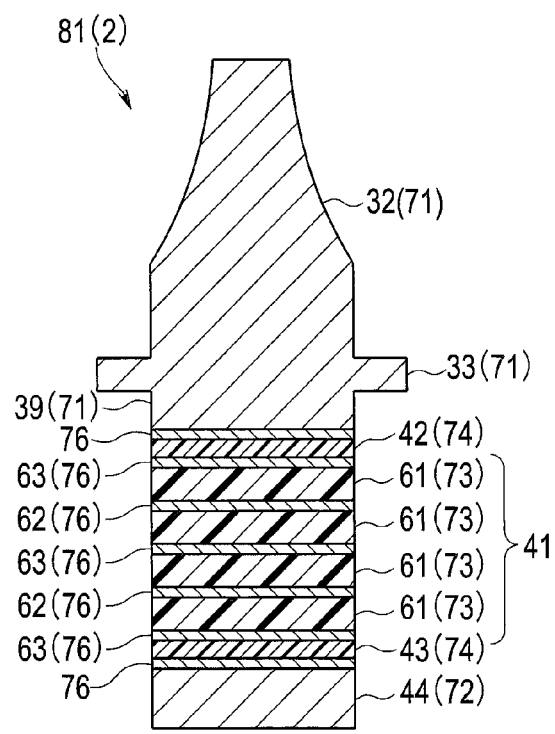
FIG. 12 is a cross-sectional view showing the ultrasound transducer according to the first embodiment of the present invention.
Figure 13:
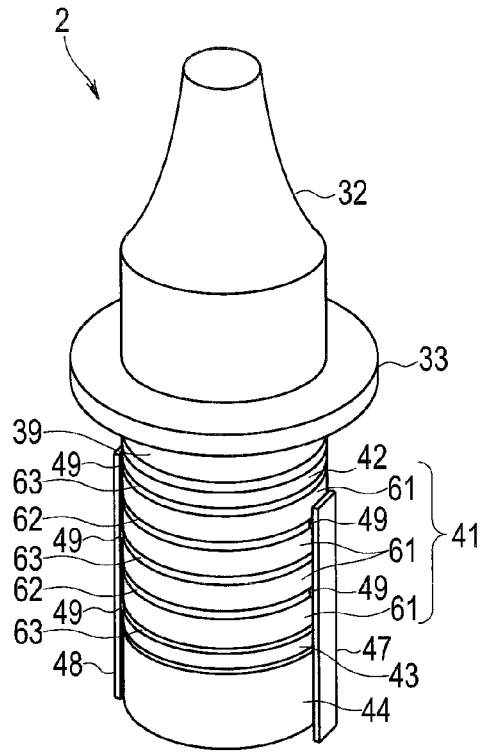
FIG. 13 is a perspective view showing the ultrasound transducer on which FPCs are connected to electrodes, according to the first embodiment of the present invention.
Figure 14:
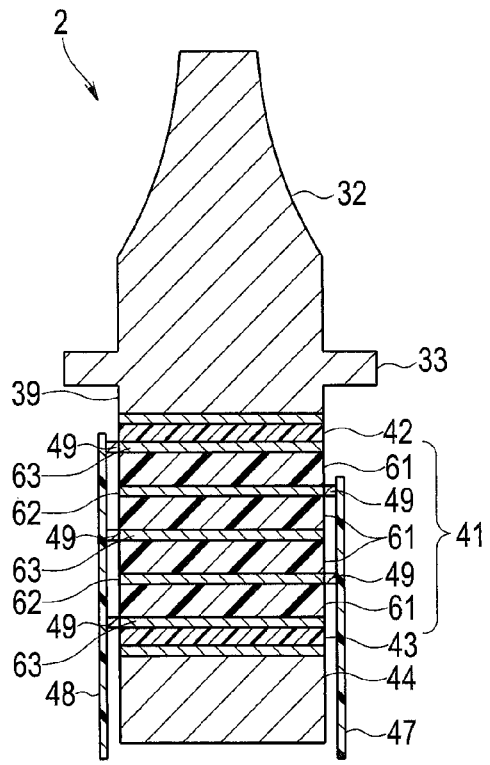
FIG. 14 is a cross-sectional view showing the ultrasound transducer on which the FPCs are connected to the electrodes, according to the first embodiment of the present invention.
Figure 15:
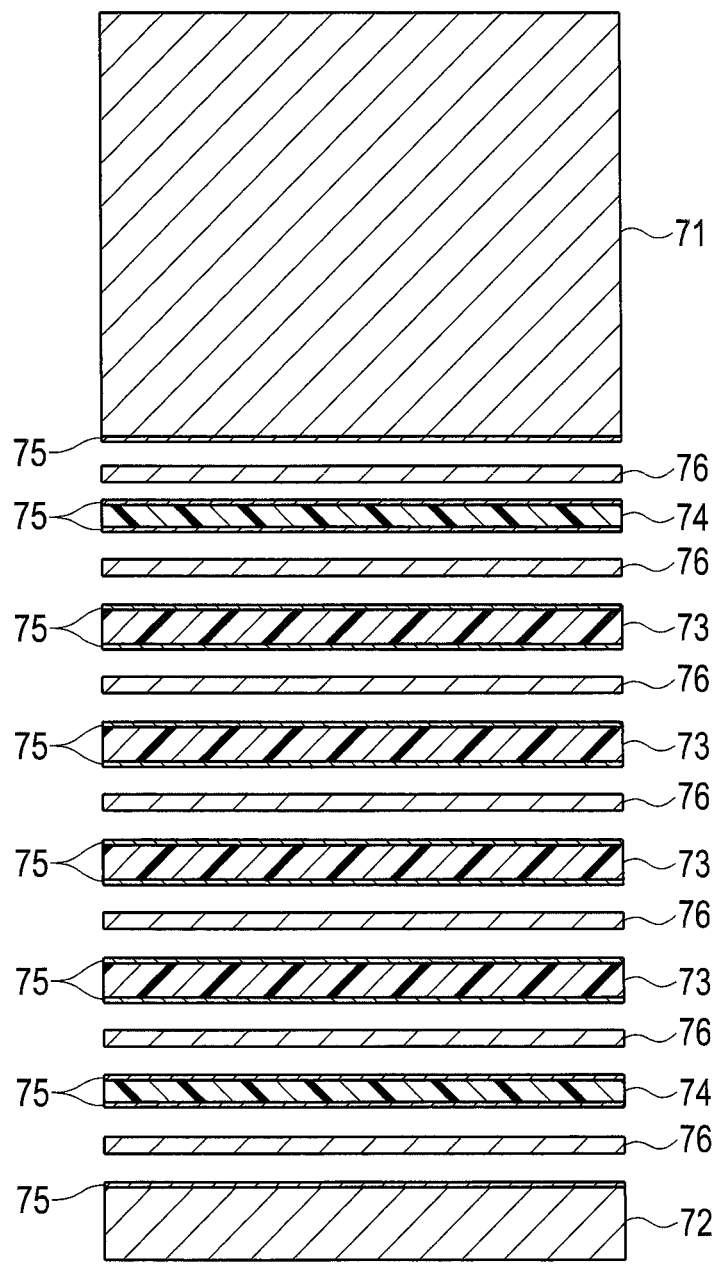
FIG. 15 is a cross-sectional view showing a configuration with various kinds of stack materials of a modification according to the first embodiment of the present invention.

FIG. 1 is a cross-sectional view showing an overall configuration of an ultrasound medical apparatus. FIG. 2 is a diagram showing a schematic configuration of a whole transducer unit. FIG. 3 is a cross-sectional view of an overall configuration of an ultrasound medical apparatus of another aspect. FIG. 4 is a perspective view showing a configuration of an ultrasound transducer. FIG. 5 is a cross-sectional view showing the configuration of the ultrasound transducer. FIG. 6 is cross-sectional views showing a configuration with various kinds of stack materials. FIG. 7 is a cross-sectional view showing a bonded block body obtained by the various kinds of stack materials being bonded with one another. FIG. 8 is a perspective view showing the bonded block body obtained by the various kinds of stack materials being bonded with one another. FIG. 9 is a perspective view showing a bonded columnar body cut out from the bonded block body. FIG. 10 is a cross-sectional view showing the bonded columnar body. FIG. 11 is a perspective view showing the ultrasound transducer with a horn formed from the bonded columnar body. FIG. 12 is a cross-sectional view showing the ultrasound transducer. FIG. 13 is a perspective view showing the ultrasound transducer on which FPCs are connected to electrodes. FIG. 14 is a cross-sectional view showing the ultrasound transducer on which the FPCs are connected to the electrodes. FIG. 15 is a cross-sectional view showing a configuration with various kinds of stack materials of a modification.

(Ultrasound Medical Apparatus)

An ultrasound medical apparatus 1 shown in FIG. 1 is provided with a transducer unit 3 having an ultrasound transducer 2 which mainly causes ultrasound vibration to occur, and a handle unit 4 for performing treatment of an affected part using the ultrasound vibration.

The handle unit 4 is provided with an operation portion 5, an insertion sheath portion 8 constituted by a long sheath tube 7, and a distal-end treatment portion 30. A proximal end portion of the insertion sheath portion 8 is attached to the operation portion 5 such that the proximal end portion can rotate in an around-axis direction. The distal-end treatment portion 30 is provided at a distal-end of the insertion sheath portion 8. The operation portion 5 of the handle unit 4 has an operation portion body 9, a fixed handle 10, a movable handle 11 and a rotating knob 12. The operation portion body 9 is formed integrally with the fixed handle 10.

On back side of a connecting portion between the operation portion body 9 and the fixed handle 10, a slit 13 is formed through which the movable handle 11 is to be inserted. An upper portion of the movable handle 11 extends to an inside of the operation portion body 9 through the slit 13. A handle stopper 14 is fixed to a lower-side end portion of the slit 13. The movable handle 11 is rotatably attached to the operation portion body 9 via a handle spindle 15. Accompanying the movable handle 11 rotating with the handle spindle 15 as a center, an operation of opening/closing the movable handle 11 relative to the fixed handle 10 is performed.

At an upper end portion of the movable handle 11, a substantially U-shaped connecting arm 16 is provided. The insertion sheath portion 8 has the sheath tube 7 and an operation pipe 17 movably inserted into an inside of the sheath tube 7 in an axial direction. At a proximal end portion of the sheath tube 7, a large diameter portion 18 having a larger diameter than that of a distal-end side portion is formed. The rotating knob 12 is fitted around the large diameter portion 18.

On an outer circumferential face of an operation pipe 19, a ring-shaped slider 20 is provided such that it is movable along the axial direction. In rear of the slider 20, a fixed ring 22 is arranged via a coil spring (elastic member) 21.

Furthermore, a proximal end portion of a grasping portion 23 is rotatably connected to a distal end portion of the operation pipe 19 via an action pin. The grasping portion 23 constitutes a treatment portion of the ultrasound medical apparatus 1 together with a distal end portion 31 of a probe 6. At a time of an operation of the operation pipe 19 moving in the axial direction, an operation of pushing/pulling the grasping portion 23 in a front/rear direction is performed via the action pin. At this time, at a time of an operation of the operation pipe 19 being operated to move to a hand side, the grasping portion 23 is rotated in a clockwise direction with a fulcrum pin as a center, via the action pin. Thereby, the grasping portion 23 rotates in a direction of coming close to the distal end portion 31 of the probe 6 (a closing direction). At this time, it is possible to grasp living tissue between the single opening type grasping portion 23 and the distal end portion 31 of the probe 6.

In a state of grasping the living tissue as described above, power is supplied from an ultrasound poser source to the ultrasound transducer 2 to cause the ultrasound transducer 2 to vibrate. The ultrasound vibration is transmitted to the distal end portion 31 of the probe 6. Then, the ultrasound vibration is used to perform treatment of the living tissue grasped between the grasping portion 23 and the distal end portion 31 of the probe 6.

(Transducer Unit)

Here, the transducer unit 3 will be described.

As shown in FIG. 2, the transducer unit 3 is configured by integrally assembling the ultrasound transducer 2 and the probe 6, which is a rod-shaped vibration transmitting member for transmitting the ultrasound vibration generated by the ultrasound transducer 2.

A horn 32 for amplifying an amplitude of the ultrasound transducer is continuously connected to the ultrasound transducer 2. The horn 32 is formed with duralumin, stainless steel or titanium alloy such as 64Ti(Ti-6AI-4V). The horn 32 is formed in such a cone shape that an outer diameter decreases as a distal end side is nearer, and an outward flange 33 is formed on a proximal-end outer circumferential portion thereof. Note that the shape of the horn 32 is not limited to a cone shape, but such an exponential shape that the outer diameter exponentially decreases as the distal end side is nearer, such a step shape that the outer diameter incrementally decreases as the distal end side is nearer, and the like are also possible. Note that a front mass 39 is integrally formed in rear of the outward flange 33.

The probe 6 has a probe body 34 formed with titanium alloy such as 64Ti(Ti-6AI-4V). On a proximal end portion side of the probe body 34, the ultrasound transducer 2 continuously connected to the horn 32, which has been described above, is arranged. The transducer unit 3 which is an integration of the probe 6 and the ultrasound transducer 2 is formed as described above. Note that the probe 6 is configured by screwing the probe body 34 and the horn 32 to each other, and the probe body 34 and the horn 32 are bonded with each other.

Ultrasound vibration generated by the ultrasound transducer 2 is transmitted to the distal end portion 31 side of the probe 6 after being amplified by the horn 32. On the distal end portion 31 of the probe 6, the treatment portion for treating living tissue is formed, which is to be described later.

Two rubber linings 35 formed in ring shapes with elastic members are attached to an outer circumferential face of the probe body 34 with an interval therebetween, at several positions which are nodal positions of vibration existing along the axial direction. Contact between the outer circumferential face of the probe body 34 and the operation pipe 19 to be described later is prevented by the rubber linings 35. That is, at a time of assembling the insertion sheath portion 8, the probe 6 as a probe integrated with transducer is inserted into an inside of the operation pipe 19. At this time, contact between the outer circumferential face of the probe body 34 and the operation pipe 19 is prevented by the rubber linings 35.

The ultrasound transducer 2 is electrically connected to a power source device body not shown, which supplies a current for generating ultrasound vibration, via an electrical cable 36. By supplying power from the power source device body to the ultrasound transducer 2 through wiring in the electrical cable 36, the ultrasound transducer 2 is driven. Note that the transducer unit 3 is provided with the ultrasound transducer 2 which generates ultrasound vibration, the horn 32 which amplifies the generated ultrasound vibration and the probe 6 which transmits the amplified ultrasound vibration.

Note that the ultrasound transducer 2 and the transducer unit 3 are not necessarily required to be housed in the operation portion body 9 as shown in FIG. 1 but may be housed in the operation pipe 19 as shown in FIG. 3. In the ultrasound medical apparatus 1 in FIG. 3, the electrical cable 36 existing between a bend preventer 52 of the ultrasound transducer 2 and a connector 38 arranged at a base of the operation portion body 9 is inserted and housed in a metallic pipe 37. Here, the connector 38 is not indispensable. A configuration is also possible in which the electrical cable 36 is extended to the inside of the operation portion body 9 and directly connected to the bend preventer 52 of the ultrasound transducer 2. By the ultrasound medical apparatus 1 as in FIG. 3, it is possible to realize further space saving of the inside the operation portion body 9. Note that functions as the ultrasound medical apparatus 1 in FIG. 3 are similar to those in FIG. 1, so description thereof will be omitted.

(Ultrasound Transducer)

Here, the ultrasound transducer 2 as an ultrasound vibration device of the present invention will be described below.

The ultrasound transducer 2 of the transducer unit 3 is configured having the horn 32 connected to the probe body 34, which is one of vibration transmitting members, by being screwed and so forth, and a stacked transducer 41 continuously connected in rear of the horn 32, in that order from a distal end of the ultrasound transducer 2, and a cover body 51 covering the stacked transducer 41 from a proximal end of the horn 32 to the electrical cable 36, as shown in FIGS. 4 and 5. Note that the cover body 51 covering the stacked transducer 41 has the bend preventer 52 covering wirings 36a and 36b which extend from the electrical cable 36 and which are electrically connected with solder or the like to contact lands of two FPCs (flexible substrates) 47 and 48 as current-carrying portions, at a proximal end portion.

Insulating layers 42 and 43 are arranged before and after the stacked transducer 41. A front side of the stacked transducer 41 is bonded with the columnar front mass 39 formed integrally with the horn 32, which is a metallic block body, via the insulating layer 42, and a rear side is bonded with a back mass 44, which is a columnar metallic block body, via the insulating layer 43. Note that the front mass 39 and the back mass 44 are formed with duralumin, stainless steel or titanium alloy such as 64Ti(Ti-6AI-4V).

In the stacked transducer 41, a plurality of here four piezoelectric single crystal element layers 61 are stacked as piezoelectric layers formed with non-lead piezoelectric single crystal plates having a heat resistance. Positive electrode layers 62 and negative electrode layers 63 are alternately interposed at both ends of the piezoelectric single crystal element layers 61 and between piezoelectric single crystal element layers 61.

(Method of Manufacturing Ultrasound Transducer)

Here, a method of manufacturing the ultrasound transducer 2 will be described below on a basis of drawings.

At a time of manufacturing the ultrasound transducer 2, metal for horn 71, metal for back mass 72, a plurality of, here four piezoelectric material wafers 73, and two insulating plates 74 are prepared first as shown in FIG. 6. Note that, as the metal for horn 71 and the metal for back mass 72, substantially columnar metallic block bodies made of duralumin, titanium alloy or stainless steel are used as described above.

The piezoelectric material wafers 73 here are formed with substantially circular plate shaped lithium niobate (LiNbO3) having a high Curie point. Insulators made of ceramics or the like and formed in a substantially circular plate shape are used as the two insulating plates 74.

Underlying metal 75 is formed as film on one face of each of the metal for horn 71 and the metal for back mass 72, both faces of the piezoelectric material wafers 73, and both faces of each of the insulating plates 74. As the underlying metal 75, Ti/Ni/Au, Cr/Ni/Au, Cr/Ni/Pd/Au or the like is used, and the film of the underlying metal 75 is formed as metallic film on both faces of the piezoelectric material wafers 73 and both faces of each of the insulating plates 74 by a method such as vapor deposition, sputtering and plating.

Then, bonding metal 76, which is AuSn eutectic solder or general non-lead solder, is provided on the underlying metal 75 of the metal for back mass 72, the underlying metal 75 on one face side of each of the piezoelectric material wafers 73, and on one face side of each of the insulating plates 74 by screen printing.

Next, the above materials are used to stack the metal for back mass 72, one of the insulating plates 74 with the bonding metal 76 positioned upward, the four piezoelectric material wafers 73 with the bonding metal 76 positioned upward, the other insulating plate 74 with the bonding metal 76 positioned upward, and the metal for horn 71 with the underlying metal 75 positioned downward in that order from a downward side of the paper, which is a proximal end side of the ultrasound transducer 2. At this time, the stack is performed so that upper and lower faces of crystal of the four piezoelectric material wafers 73 are alternately reversed between adjoining wafers among the respective wafers. That is, the bonding metal 76 is screen-printed on an upper face side of crystal of two piezoelectric material wafers 73 and on a lower face of crystal of two piezoelectric material wafers 73, and the stack is performed so that the upper and lower faces of the crystal of the four piezoelectric material wafers 73 are alternately reversed between adjoining wafers as described above.

A stacked body in which the respective materials are stacked as described above is cooled slowly after being heated to be at a temperature at which each of the pieces of bonding metal 76 fuses, for example, about 200° C. to 300° C. Thereby, each of the metal for horn 71, one of the insulating plates 74, the four piezoelectric material wafers 73, the other insulating plates 74 and the metal for back mass 72 from an upward of the paper is bonded relative to a stack direction by fusion of the bonding metal 76. Note that, since the underlying metal 75 shows favorable adhesiveness of each material and shows favorable wettability at a time of fusion of the bonding metal 76, each material is stably bonded.

Thus, as shown in FIGS. 7 and 8, a bonded block body, a substantially columnar bonded block body 80 is formed which is integrated so that the bonding metal 76 is stacked between the respective piezoelectric material wafers 73 and the respective insulating plates 74. It is assumed that, at a time of the heating described above, predetermined uniform pressurization is performed from a distal end side of the bonded block body 80 (an upper portion side of the paper), that is, from the metal for horn 71 side as necessary. Note that a thickness of the underlying metal 75 is so thin that even a whole thickness of all the layers is several um or so, and, therefore, the underlying metal 75 is not shown in FIG. 7 and succeeding drawings.

Next, a plurality of bonded columnar bodies 81 as shown in FIGS. 9 and 10 are cut out from one bonded block body 80 fabricated as described above by machining such as grinding and cutting processing. Note that, at this time, the outward flange 33 described above which is for holding the transducer unit 3 and the front mass 39, which is to be continuously connected to the rear of the outward flange 33, are integrally machined from the metal for horn 71.

Then, machining of the metal for horn 71 of the bonded columnar body 81 by grinding, cutting processing and the like is performed so that the metal for horn 71 is to be in a tapered shape of becoming gradually thin toward a distal end portion side of the transducer unit 3 (the upper portion side of the paper) as shown in FIGS. 11 and 12, and the horn 32 described above which has an effect of amplifying an amplitude of ultrasound vibration is machined. Note that a female screw hole not shown, which is for screwing the probe body 34 from a distal end face toward an inside direction, is tapped on the horn 32.

In this way, the horn 32, the outward flange 33 and the front mass 39 are formed from the metal for horn 71 of the bonded columnar body 81 by machining. The two insulating plates 74 of the bonded columnar body 81 constitute the insulating layers 42 and 43 of the ultrasound transducer 2, and the plurality of, here four piezoelectric material wafers 73 constitute the piezoelectric single crystal element layers 61 of the ultrasound transducer 2. Furthermore, pieces of bonding metal 76 sandwiching the four piezoelectric material wafers 73 of the bonded columnar body 81 constitute the positive electrode layers 62 or the negative electrode layers 63 of the ultrasound transducer 2, and the metal for back mass 72 constitutes the back mass 44 of the ultrasound transducer 2. As described above, the plurality of bonded columnar bodies 81 are cut out from the bonded block body 80, and the ultrasound transducer 2 is individualized and manufactured from one bonded columnar body 81 by batch processing. Note that the bonding metal 76 between the metal for horn 71 or the metal for back mass 72 and any of the insulating plates 74 does not constitute a positive electrode layer 62 or a negative electrode layer 63, but it is for bonding the metal for horn 71 or the metal for back mass 72 and the insulating plate 74.

In the ultrasound transducer 2, two FPCs 47 and 48 are electrically connected to a positive electrode layer 62 or a negative electrode layer 63 sandwiching each piezoelectric single crystal element layer 61 via electrical connection portions 49 such as solder for electrical connection to each piezoelectric single crystal element layer 61 as shown in FIGS. 13 and 14, so that the electrical connection to each piezoelectric single crystal element layer 61 is established. Note that the FPCs 47 and 48 electrically connect the alternately stacked negative electrode layers 63 with one another or connect the alternately stacked positive electrode layers 62 with one another.

By a process of manufacturing the ultrasound transducer 2 described above, the horn 32 in which the outward flange 33 and the front mass 39 are integrally formed, the insulating layer 42, each piezoelectric single crystal element layer 61, the negative electrode layers 63, the positive electrode layers 62, the insulating layer 43 and the back mass 44 are integrally manufactured. Then, by applying a driving signal to each piezoelectric single crystal element layer 61 via the FPCs 47 and 48 which are electrically connected to side faces of the positive electrode layers 62 or the negative electrode layers 63 via the electrical connection portions 49 such as solder, the ultrasound transducer 2 is completed which causes the whole ultrasound transducer 2 to ultrasound-vibrate.

Note that, in the ultrasound transducer 2, the driving signal applied to the positive electrode layers 62 from the FPC 47 on a positive electrode side flows from the negative electrode layers 63 to the FPC 48 on a negative electrode side (GND side) via the respective piezoelectric single crystal element layers 61. Therefore, though the ultrasound transducer 2 is configured being provided with the insulating layers 42 and 43 here, the driving signal does not flow in a case of a configuration in which the front mass 39 and the back mass 44 are in contact with the negative electrode layers 63, even if the insulating layers 42 and 43 are not especially provided. That is, if the ultrasound transducer 2 is configured such that an even number of piezoelectric single crystal element layers 61 are provided, and the negative electrode layers 63 are arranged at both ends of the piezoelectric single crystal element layers 61, that is, at both ends of the stacked transducer 41, as in the present embodiment, the insulating layers 42 and 43 are not necessarily required to be provided.

Lithium niobate (LiNbO3) is used for each piezoelectric single crystal element layer 61 here, and the Curie point is about 1150° C. A melting point of the bonding metal 76, such as AuSn eutectic solder and general non-lead solder, constituting the positive electrode layers 62 or the negative electrode layers 63 is about 200 to 300° C., half the Curie point of Lithium niobate (LiNbO3) (about 1150° C.) or below (here, ⅓ or below). Therefore, even if heat treatment is performed to bond the respective stack materials at a temperature up to a temperature at which the bonding metal 76 fuses (about 200 to 300° C.) or so, polarization of each of the piezoelectric material wafers 73 to be the piezoelectric single crystal element layers 61 does not deteriorate, and it is possible to immediately use the ultrasound transducer 2 as an ultrasound transducer 2 of a Langevin transducer without performing a re-polarization process after assembling and machining processes.

Furthermore, it is desirable that a thermal expansion coefficient of the metal for horn 71 and the metal for back mass 72 are as close to a thermal expansion coefficient of a piezoelectric single crystal plate as possible in order to prevent a crack of each piezoelectric material wafer 73 due to thermal stress caused by thermal expansion coefficient difference at a time of cooling after heating for bonding of the stack materials. Therefore, non-lead lithium niobate (LiNbO3) is used for the piezoelectric material wafers 73 here as described above. Since the thermal expansion coefficient is about 8 to 15 ppm depending on a crystal direction, titanium alloy or stainless steel having a thermal expansion coefficient close to the value of about 8 to 15 ppm is especially desirable as the material of the metal for horn 71 and the metal for back mass 72.

As described above, in the present embodiment, the piezoelectric material wafers 73 in a shape larger than a final shape of the ultrasound transducer 2 which is a manufacture object, to be the piezoelectric single crystal element layers 61; the bonding metal 76 to be the positive electrode layers 62 or the negative electrode layers 63; metal blocks of the metal for horn 71 to be the horn 32, the outward flange 33 and the front mass 39; a metal block of the metal for back mass 72 to be the back mass 44; and the insulating plates 74 to be the insulating layers 42 and 43 are stacked. Then, by arranging the bonding metal 76 made of metallic material as a bonding portion, respectively between the stacked layers, heating these to increase a temperature to be the melting point of the bonding metal 76 or above, and then cooling these, the bonded block body 80 obtained by bonding and integrating these is formed first.

Note that, as the metallic material used as the bonding metal 76 here, material having a melting point equal to or below half the Curie point of the piezoelectric material wafers 73 is used, and, therefore, it is possible to perform bonding without causing depolarization of the piezoelectric material wafers 73 even when the bonding is performed by melting the metal. That is, it is possible to easily manufacture the ultrasound transducer 2 which can be driven without performing repolarization of the piezoelectric single crystal element layers 61 after machining from the bonded block body 80. It is possible to manufacture the ultrasound transducers 2, which are a plurality of Langevin transducers, from one bonded block body 80 by performing batch machining from the bonded block body 80, a bonded body in which the respective stack materials are integrated. Lastly, the FPCs 47 and 48, which are to be electrodes for driving the piezoelectric transducer, are attached to the side faces of the positive electrode layers 62 or the negative electrode layers 63 of the cut-out ultrasound transducers 2 so that an electrical signal for driving can be applied to each piezoelectric transducer.

As described above, by performing batch processing and individualization after bonding the respective stack materials, it is possible to reduce the number of times of machining and enable cost saving in comparison with a case of individually machining the ultrasound transducers 2 one by one. There is also an advantage that, since end portions of the piezoelectric material wafers 73 to be the piezoelectric single crystal element layers 61 are not exposed at a time of machining, chipping does not easily occur. As a result, the ultrasound transducer 2 of the present embodiment makes it possible to reduce a processing cost of the piezoelectric material wafers 73 using non-lead lithium niobate (LiNbO3) to fabricate the piezoelectric material wafers 73 inexpensively.

Note that, though the configuration has been shown above in which the bonding metal 76, which is AuSn eutectic solder or general non-lead solder, is provided by screen printing on the underlying metal 75 on one face side of the piezoelectric material wafers 73 and on the underlying metal 75 on one face side of one of the insulating plate 74, this is not limiting, and the bonding metal 76 may be arranged respectively between the metal for horn 71, the metal for back mass 72, the respective piezoelectric material wafers 73 and the respective insulating plates 74 in a form of a ribbon (a metallic ribbon) as shown in FIG. 15.

Second Embodiment

Next, a second embodiment of the present invention will be described below on a basis of drawings.

Figure 16:
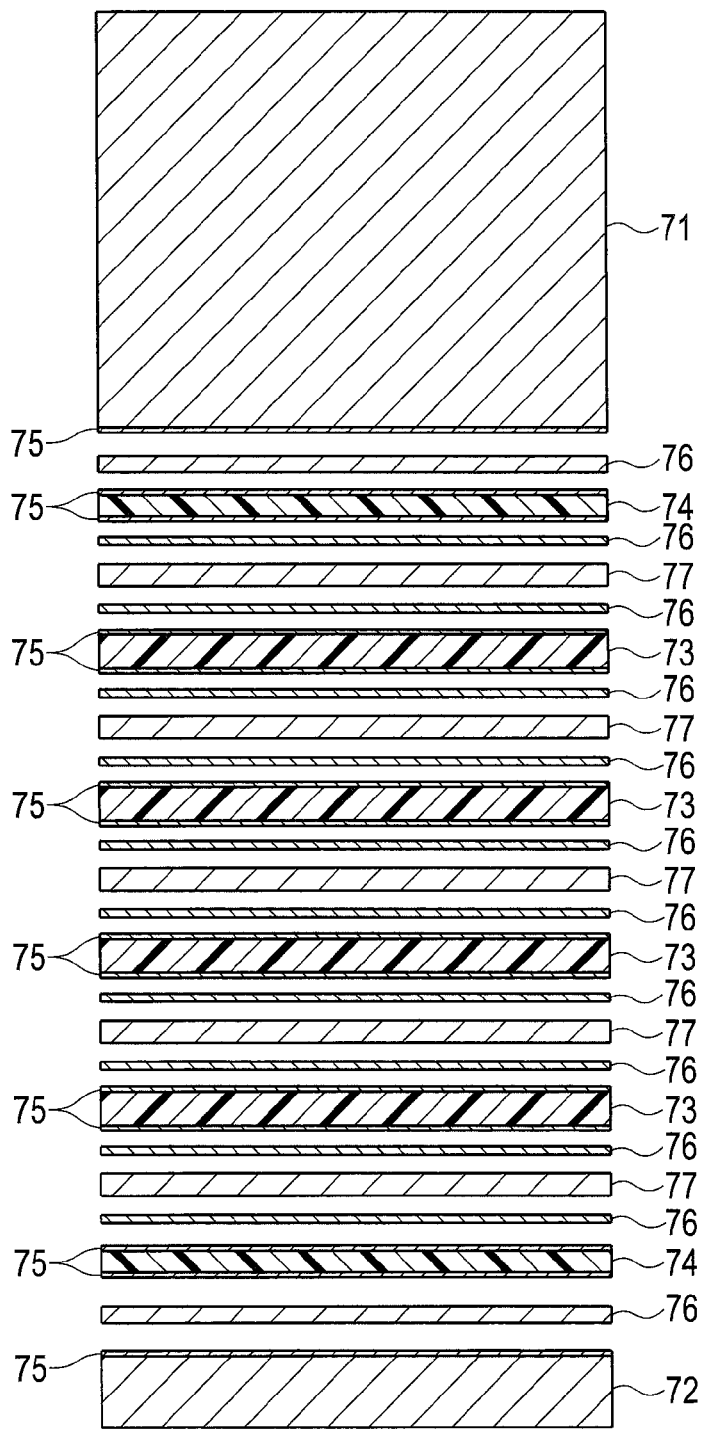
FIG. 16 is a cross-sectional view showing a configuration with various kinds of stack materials according to a second embodiment of the present invention.

FIG. 16 is cross-sectional view showing a configuration with various kinds of stack materials. FIG. 17 is a perspective view showing an ultrasound transducer on which FPCs are connected to electrodes. FIG. 18 is a cross-sectional view showing the ultrasound transducer on which the FPCs are connected to the electrodes.

Note that, in description of the present embodiment, same reference numerals are used for the components described in the first embodiment, and detailed description of the components will be omitted.

In the first embodiment described above, a configuration is assumed in which the FPCs 47 and 48 are electrically connected and mechanically fixed to the side faces of the positive electrode layers 62 or the negative electrode layers 63 formed with the bonding metal 76 via the electrical connection portions 49. In addition to the configuration, the electrical connection portions 49 and the positive electrode layers 62 or the negative electrode layers 63 are required to have a certain size (thickness) in order to secure necessary strength for mechanical fixation, and, therefore, the bonding metal 76 to be the positive electrode layers 62 or the negative electrode layers 63 are required to have a certain level of thickness. It is desirable that the thickness is larger than a minimum thickness required for bonding. On the contrary, for example, in a case of using AuSn which includes gold as the bonding metal 76, material cost is high because expensive Au is included, and it is desirable to suppress the thickness of the bonding metal 76 to the minimum thickness required for bonding.

Therefore, in the present embodiment, a thickness of the positive electrode layers 62 or the negative electrode layers 63 is secured by providing metallic spacers 77 having a predetermined thickness and formed with metallic material which is more inexpensive than the bonding metal 76, for example, copper (Cu) as shown in FIG. 16.

More specifically, a metallic spacer 77 is arranged, with the bonding metal 76 arranged on each of both sides of the metallic spacer 77, between an insulating plate 74 and each piezoelectric material wafer 73. To describe this in detail, a metallic spacer 77 is arranged between an insulating plate 74 and each piezoelectric material wafer 73 such that the metallic spacer 77 is sandwiched between two ribbon-formed pieces of bonding metal 76 here, and the respective materials are stacked.

Note that, here also, similarly as in the first embodiment, the underlying metal 75 is formed as film on both sides of each insulating plate 74 and each piezoelectric material wafer 73, the underlying metal 75 being such that the bonding metal 76, the metal for horn 71 or the metal for back mass 72 and the insulating plates 74 or the piezoelectric material wafers 73 to be bonded show favorable adhesiveness and favorable wettability at the time of fusion.

Copper (Cu) or the like is used for the metallic spacers 77 as described above. When combination of materials of the metallic spacers 77 and the bonding metal 76 is copper (Cu) and general non-lead solder, favorable bondability is shown, and, therefore, a configuration here is such that it is not necessary to form the film of the underlying metal 75 on the metallic spacers 77.

Note that the film of the underlying metal 75 may be formed on the metallic spacers 77 as necessary depending on the combination of the materials of the metallic spacers 77 and the bonding metal 76. Though the bonding metal 76 is assumed to be in a ribbon form here, the bonding metal 76 may be screen-printed as paste depending on the thickness of the metallic spacers 77. Especially, since it is difficult to stack the respective materials after screen-printing the bonding metal 76 as paste if the thickness of the metallic spacers 77 is thin, it is desirable that the bonding metal 76 is in a ribbon form in that case.

In the embodiment described above also, similarly as in the first embodiment, a stacked body constituted by the respective materials is cooled slowly after being heated to be at the temperature at which the bonding metal 76 fuses, and each of the metal for horn 71, one of the insulating plates 74, each piezoelectric material wafer 73, each of the pieces of bonding metal 76, each metallic spacer 77, the other insulating plate 74 and the metal for back mass 72 is bonded. Here also, each material is bonded while the underlying metal 75 shows favorable adhesiveness of each material, and favorable wettability at the time of fusion of the bonding metal 76.

In this way, by a metallic spacer 77 being integrated on and under each piezoelectric material wafer 73 such that the metallic spacer 77 is sandwiched between the pieces of bonding metal 76, a bonded block body (80) not shown here is formed similarly as in the first embodiment. Then, similarly as in the first embodiment, a plurality of bonded columnar bodies (81) not shown here are cut out from the bonded block body by machining such as cutting. Then, the outward flange 33 and the front mass 39 continuously connected to the rear of the outward flange 33 are integrally machined on the metal for horn 71.

In this way, in the present embodiment, metallic spacers 77 each of which is provided between two pieces of bonding metal 76 are arranged so as to sandwich each piezoelectric material wafer 73; each metallic spacer 77 constitutes the positive electrode layer 62 or the negative electrode layer 63; and a plurality of bonded columnar bodies 81 are cut out from the bonded block body 80. In this way, the ultrasound transducers 2 are individualized and manufactured by batch processing. Note that, other components of the ultrasound transducer 2 are similar to those in the first embodiment.

In the ultrasound transducer 2, similarly as in the first embodiment, the two FPCs 47 and 48 are electrically connected to the positive electrode layers 62 or the negative electrode layers 63 having a sufficient thickness due to three layers of two pieces of bonding metal 76 and a metallic spacer 77 via the electrical connection portions 49 such as solder for electrical connection to each piezoelectric single crystal element layer 61 as shown in FIGS. 17 and 18, so that the electrical connection to each piezoelectric single crystal element layer 61 is established. Note that, here also, the thickness of the underlying metal 75 is so thin that even the whole thickness of all the layers is several um or so, and, therefore, the underlying metal 75 is not shown in FIGS. 17 and 18.

According to the above description, the ultrasound transducer 2 of the present embodiment is configured such that a thickness of the positive electrode layers 62 or the negative electrode layers 63 to which the electrical connection portions 49 are connected is sufficiently secured to secure necessary strength for mechanical fixation, in addition to the effects of the first embodiment. Furthermore, in the case of using AuSn or the like which includes gold as the bonding metal 76, it is possible to suppress the thickness of the bonding metal 76 and secure the thickness of the positive electrode layers 62 or the negative electrode layers 63 by the metallic spacers 77 formed with inexpensive material, copper (Cu) here, and, therefore, it is possible to reduce a manufacture cost of the ultrasound transducer 2. In the case of using copper (Cu) as the metallic spacers 77, the electrical connection portions 49 can be formed by directly applying solder to side face portions of the positive electrode layers 62 or the negative electrode layers 63 configured by the metallic spacers 77.

The ultrasound transducer 2 of the present embodiment configured as described above can realize both of reduction in material used and cost saving due to causing the bonding metal 76 to be thin film, and security of a distance between adjoining piezoelectric single crystal element layers 61 required for mechanical strength of the electrical connection portions 49.

Third Embodiment

Next, a third embodiment of the present invention will be described below on a basis of drawings.

Figure 19:
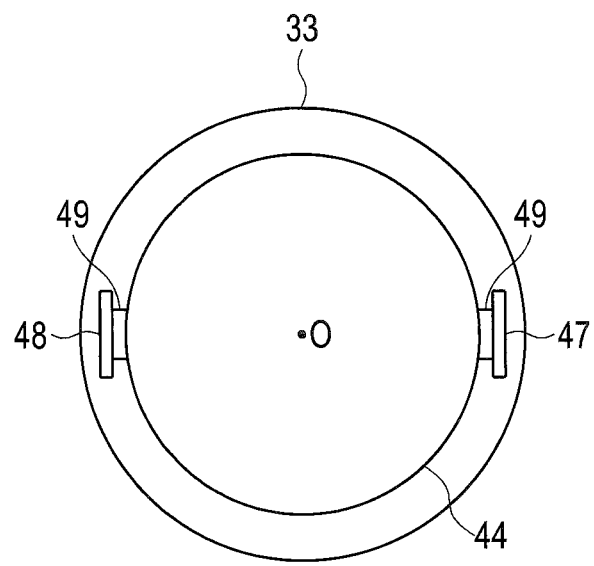
FIG. 19 is a rear view showing an example of an ultrasound transducer according to a third embodiment of the present invention.
Figure 20:
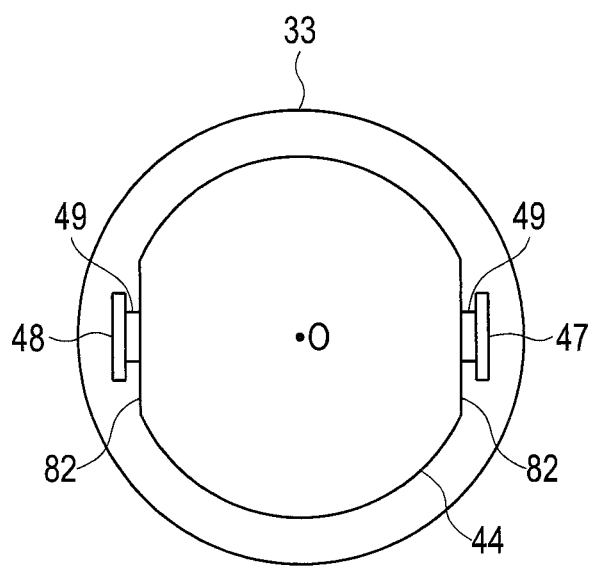
FIG. 20 is a rear view showing an example of two flat portions being formed on the ultrasound transducer, according to the third embodiment of the present invention.
Figure 21:
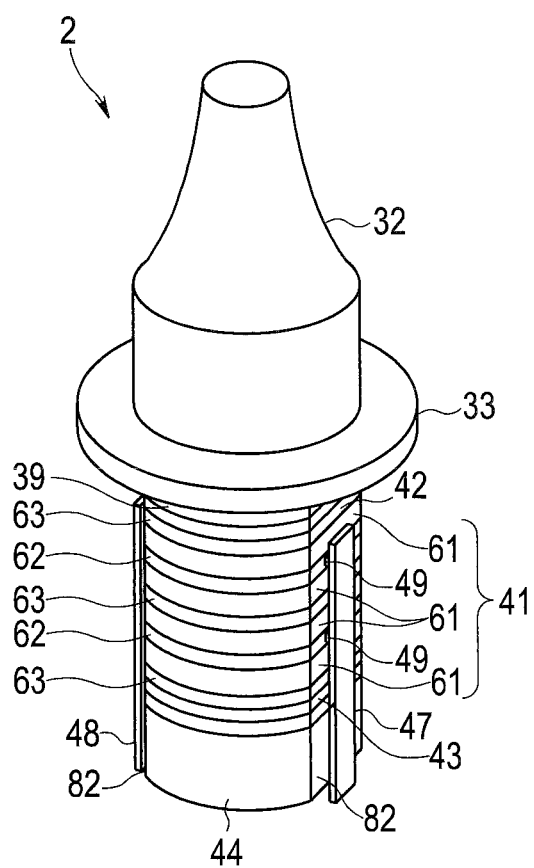
FIG. 21 is a perspective view showing the ultrasound transducer in FIG. 20 on which FPCs are connected to electrodes according to the third embodiment of the present invention.
Figure 22:
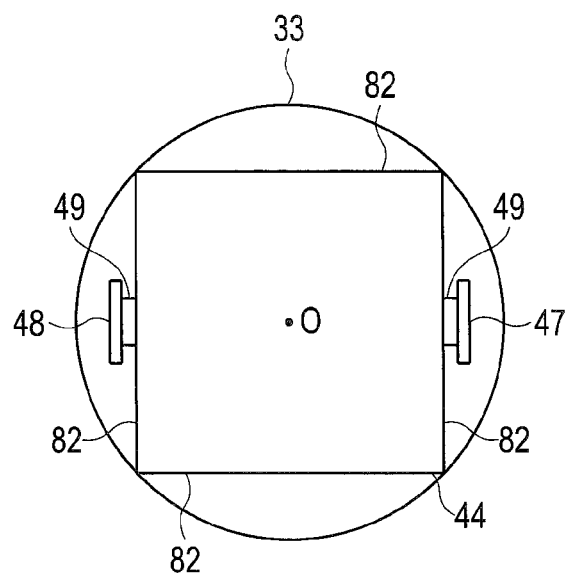
FIG. 22 is a rear view showing an example of four flat portions being formed on the ultrasound transducer according to the third embodiment of the present invention.
Figure 23:
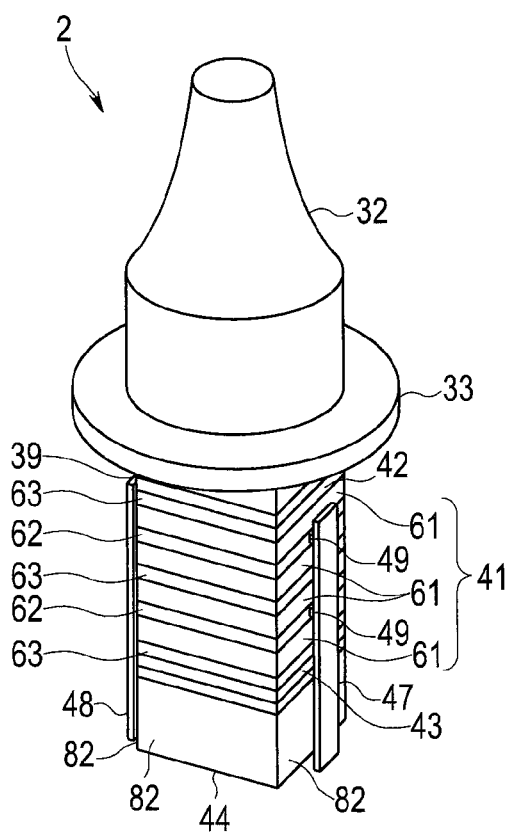
FIG. 23 is a perspective view showing the ultrasound transducer in FIG. 22 to which the FPCs are connected, according to the third embodiment of the present invention.

FIG. 19 is a rear view showing an example of an ultrasound transducer. FIG. 20 is a rear view showing an example of two flat portions being formed on the ultrasound transducer. FIG. 21 is a perspective view showing the ultrasound transducer in FIG. 20 on which FPCs are connected to electrodes. FIG. 22 is a rear view showing an example of four flat portions being formed on the ultrasound transducer. FIG. 23 is a perspective view showing the ultrasound transducer in FIG. 22 to which the FPCs are connected.

Note that, in description of the present embodiment, same reference numerals are used for the components described in the first and second embodiments, and detailed description of the components will be omitted.

It is desirable that an external shape of a section of the ultrasound transducer 2, which is the Langevin transducer of each of the embodiments described above, is circular as shown in FIG. 19 when seen from a vibration direction (front/rear direction), from a viewpoint of symmetry relative to a central axis O of the vibration direction. In the case where the external shape of the section is circular, however, it is necessary to use a jig for preventing rolling of the ultrasound transducer 2 and a jig for determining positions for fixing the FPCs 47 and 48 at a time of connecting the FPCs 47 and 48 to the positive electrode layers 62 or the negative electrode layers 63 via the electrical connection portions 49.

Further, in order to fix the electrical connection portions 49 at a side periphery of the positive electrode layers 62 or the negative electrode layers 63, it is necessary to fix the electrical connection portions 49 to the ultrasound transducer 2 in a state that shapes of the electrical connection portions 49 are along a circular arc shape corresponding to the positive electrode layers 62 or the negative electrode layers 63 or in a state that the FPCs 47 and 48 are bent to be along the circular arc shape of the positive electrode layers 62 or the negative electrode layers 63. Therefore, there is a matter of concern that reliability of electrical connection to the positive electrode layers 62 or the negative electrode layers 63 by the electrical connection portions 49 and workability of a process of forming the electrical connection portions 49 may deteriorate.

Thus, in the present embodiment, by providing the stacked transducer 41, the front mass 39 and the back mass 44, which are a part of the ultrasound transducer 2, with flat portions 82 and fixing the electrical connection portions 49 to the flat portions 82 as shown in FIGS. 20 and 21, in a process of individualizing the bonded columnar bodies (81) from the bonded block body (80), it is possible to improve the workability at a time of connecting the FPCs 47 and 48, reduce an assembly cost, and improve the connection reliability of the electrical connection portions 49. Furthermore, as shown in FIGS. 22 and 23, four side faces of the stacked transducer 41, the front mass 39 and the back mass 44 may be constituted only by the flat portions 82 so that the external shape of the section when seen from the vibration direction (front/rear direction) of the ultrasound transducer 2 is rectangular.

Note that, the configuration of the present embodiment can be, of course, applied not only to the first embodiment but also to the ultrasound transducer 2 in which the positive electrode layers 62 and the negative electrode layers 63 are formed with use of the metallic spacers 77 of the second embodiment.

The inventions described in the above embodiments are not limited to the embodiments and modifications. In addition, various changes can be made at a stage of practicing the inventions within a range not departing from the spirit from the inventions. Furthermore, the above embodiments include inventions at various stages, and various inventions can be extracted by appropriate combination of constituent features among the plurality of disclosed constituent features.

For example, when a stated problem can be solved and stated effects can be obtained even if some constituent features are deleted from all constituent features described in the embodiments, a configuration from which the constituent features have been deleted can be extracted as an invention.

In the embodiments described above, it has been described that, by cutting out and individualizing a plurality of bonded columnar bodies 81 from one bonded block body 80 by machining such as grinding and cutting processing, the bonded columnar bodies 81 are fabricated. However, the process is not limiting, and it is also possible to, by using metallic blocks, insulating plates, piezoelectric single crystal elements individualized in advance, arranging positive electrode plates and negative electrode plates at both ends of the piezoelectric single crystal elements to which voltage is to be applied, and bonding and integrating those with bonding metal, fabricate a bonded columnar body and cause the bonded columnar body to be an ultrasound vibration device. The positive electrode plates and the negative electrode plates in the case of fabricating the bonded columnar body by such a process can be in such a shape that terminal portions project to an outside as shown in FIG. 5 in Patent Literature 1, and, thereby, it becomes easier to electrically connect the positive electrode plates with one another or the negative electrode plates with one another.

What is claimed is:

1. An ultrasound vibration device comprising a stacked transducer in which a plurality of piezoelectric single crystal element layers are stacked between two metal blocks, wherein
at least each of the plurality of piezoelectric single crystal element layers is fusion-bonded relative to a stack direction by bonding metal having a melting point corresponding to half a Curie point of the plurality of piezoelectric single crystal element layers or below.

2. The ultrasound vibration device according to claim 1, wherein the bonding metal constitutes a plurality of electrode layers stacked among the plurality of piezoelectric single crystal element layers.

3. The ultrasound vibration device according to claim 1, wherein a plurality of metallic spacers having a predetermined thickness are stacked among the plurality of the piezoelectric single crystal element layers, and the plurality of metallic spacers and the plurality of piezoelectric single crystal element layers are fusion-bonded relative to the stack direction by the bonding metal, so that the plurality of metallic spacers constitute the plurality of electrode layers stacked among the plurality of the piezoelectric single crystal element layers.

4. The ultrasound vibration device according to claim 1, comprising a current-carrying portion electrically connecting positive electrodes with one another or negative electrodes with one another of the plurality of electrode layers, wherein
  a side face of the stacked transducer where the current-carrying portion is electrically connected to the positive electrodes or the negative electrodes is formed as a plane.

5. The ultrasound vibration device according to claim 1, wherein the plurality of piezoelectric single crystal element layers are formed with lithium niobate, and AuSn eutectic solder or non-lead solder having a melting point corresponding to half a Curie point of the lithium niobate or below is used as the bonding metal.

6. A method of manufacturing the ultrasound vibration device according to claim 1, comprising:
  stacking a first metal block of the two metal blocks, a plurality of piezoelectric single crystal wafers, and a second metal block of the two metal blocks by providing the bonding metal therebetween respectively;
  forming an integrated block body by slowly cooling a stacked body constituted by the first metal block, the plurality of piezoelectric single crystal wafers, the second metal block and the bonding metal after heating the stacked body to be at the melting point of the bonding metal to fusion-bond the first metal block, the plurality of piezoelectric single crystal wafers and the second metal block in a stack direction by the bonding metal;
  cutting out a plurality of columnar bodies from the bonded block body by machining; and
  machining a horn for amplifying ultrasound vibration on a portion of the first metal block of the columnar body.

7. The method of manufacturing the ultrasound vibration device according to claim 6, wherein the bonding metal is provided on one face of the first metal block, the plurality of piezoelectric single crystal wafers or the second metal block by screen printing.

8. The method of manufacturing the ultrasound vibration device according to claim 6, wherein the bonding metal is a metallic ribbon and is provided respectively between the first metal block, the plurality of piezoelectric single crystal wafers and the second metal block.

9. An ultrasound medical apparatus comprising:
  the ultrasound vibration device according to claim 1; and
  a probe distal end portion to which ultrasound vibration generated by the ultrasound vibration device is transmitted and which treats living tissue.

* * * * *